(12) United States Patent
Woodward et al.

(10) Patent No.: US 9,820,954 B2
(45) Date of Patent: Nov. 21, 2017

(54) QUANTITATIVE PERI-ORBITAL APPLICATION OF OPHTHALMOLOGY DRUGS

(71) Applicant: JENIVISION INC., Irvine, CA (US)

(72) Inventors: David F. Woodward, Lake Forest, CA (US); Weizhen Wang, Irvine, CA (US)

(73) Assignee: JENIVISION INC., Irvine, CA (US)

( * ) Notice: Subject to any disclaimer, the term of this patent is extended or adjusted under 35 U.S.C. 154(b) by 0 days.

(21) Appl. No.: 14/829,789

(22) Filed: Aug. 19, 2015

(65) Prior Publication Data

US 2017/0049734 A1 Feb. 23, 2017

(51) Int. Cl.
*A61K 31/196* (2006.01)
*A61K 9/00* (2006.01)

(52) U.S. Cl.
CPC .......... *A61K 31/196* (2013.01); *A61K 9/0048* (2013.01)

(58) Field of Classification Search
CPC .................................................. A61K 31/196
See application file for complete search history.

(56) References Cited

U.S. PATENT DOCUMENTS

| | | | |
|---|---|---|---|
| 3,990,444 A | 11/1976 | Guy | |
| 4,131,115 A | 12/1978 | Sung | |
| 4,281,654 A | 8/1981 | Shell | |
| 4,655,767 A | 4/1987 | Woodard | |
| 4,839,342 A | 6/1989 | Kaswan | |
| 5,411,952 A | 5/1995 | Kaswan | |
| 6,254,860 B1 | 7/2001 | Garst | |
| 6,331,313 B1 | 12/2001 | Wong | |
| 6,342,250 B1 | 1/2002 | Masters | |
| 6,350,442 B2 | 2/2002 | Garst | |
| 7,226,435 B2 | 6/2007 | Darnell | |
| 7,326,732 B2 | 2/2008 | Oxford | |
| 7,655,625 B2 | 2/2010 | Brin | |
| 7,662,839 B2 | 2/2010 | Oxford | |
| 7,803,841 B2 | 9/2010 | Oxford | |
| 8,187,311 B2 | 5/2012 | Korb | |
| 8,685,439 B2 | 4/2014 | Chapin et al. | |
| 8,785,394 B2 | 7/2014 | Blanda et al. | |
| 8,900,626 B2 | 12/2014 | Ogawa et al. | |
| 9,034,830 B2 | 5/2015 | Nanduri et al. | |
| 2007/0051362 A1 | 3/2007 | Sullivan | |
| 2009/0318422 A1 | 12/2009 | Isowaki | |
| 2010/0145303 A1 | 6/2010 | Yodfat | |
| 2010/0331410 A1 | 12/2010 | Coleman | |
| 2011/0104083 A1 | 5/2011 | Nanduri | |
| 2011/0104206 A1 | 5/2011 | Nanduri | |
| 2012/0003296 A1 | 1/2012 | Shantha | |
| 2012/0059401 A1 | 3/2012 | Konstantino | |
| 2013/0085472 A1 | 4/2013 | Shaari | |
| 2014/0296158 A1 | 10/2014 | Blanda | |

FOREIGN PATENT DOCUMENTS

| | | |
|---|---|---|
| AU | 2008325214 A1 | 9/2009 |
| CN | 203379477 U | 1/2014 |
| WO | WO1989001772 A1 | 3/1989 |
| WO | WO1995031211 A1 | 11/1995 |
| WO | WO2000061168 | 10/2000 |
| WO | WO2009061431 | 7/2009 |
| WO | WO2012020261 | 2/2012 |
| WO | WO2014045300 A2 | 3/2014 |
| WO | WO2013074610 | 7/2014 |

OTHER PUBLICATIONS

Wolf, Clinics in Dermatology (2014) 32, 131-140.*

* cited by examiner

*Primary Examiner* — Zohreh Fay
(74) *Attorney, Agent, or Firm* — Wilson Sonsini Goodrich & Rosati

(57) ABSTRACT

The present invention is directed methods of lowering intraocular pressure in a patient suffering from elevated intraocular pressure or glaucoma and treating ocular disease by administering a drug to the periorbital skin of the patient.

29 Claims, 2 Drawing Sheets

QUANTITATIVE PERI-ORBITAL APPLICATION OF OPHTHALMOLOGY DRUGS

FIELD OF THE INVENTION

The present invention is directed to compounds, compositions and methods of administration for treating elevated intraocular pressure ("IOP") and glaucoma which provides long duration IOP reduction from a single administration and/or multiple administrations of an IOP lowering drug. The present invention is also directed to novel methods of treatment of ophthalmological diseases by applying therapeutic agents to the surface of the periorbital skin surrounding the bulbus oculi or globe of the eye. The present invention is also directed to novel devices for administering drugs to the eye through the periorbital skin.

BACKGROUND OF THE INVENTION

Treatment of diseases of the ocular anterior segment and ocular surface of the eye are traditionally treated by self-application of topical drops from drug solution or other vehicles to the surface of the eye. However, self-administration of eye drops to the eye is both inconvenient and inefficient, particularly with elderly and pediatric patients because the eye drops must be self-administered daily or multiple times daily to effectively treat the disease or condition. Many patients have an aversion to self-administering topical eye drops. In cases where the drug is in the form of a suspension or an emulsion, temporary blurred vision often results from administration. Topically applied drugs may also result in unwanted ocular side effects such as general discomfort, "burning", "stinging", ocular surface redness, hyperemia, and foreign body sensation. All of these factors contribute to a lack of compliance with topical eye drops in ocular drug therapy, particularly in the case of glaucoma where therapeutic intervention is life-long and continuous.

Data demonstrate that many patients are unable to self-administer eye drops to effectively treat their disease or condition, particularly the elderly and pediatric patients. Hennessy A. L. et al. "A Video Study of Drop Instillation in Both Glaucoma and Retina Patients with Visual Impairment." *Am. J. Ophthalmol.* 2011; 152(6):982-988. Patient questionnaires have shown that patients are unable to effectively self-dose and administer eye drops accurately and as prescribed by physicians. Robin, et al. "Adherence in glaucoma: objective measurements of once-daily and adjunctive medication use." *Am. J. Ophthalmol.* 2007; 144(4):533-540. These studies have also demonstrated that only 71% of 204 glaucoma patients were able to properly administer a drop into the eye, and only 39% of patients did so without touching the bottle to the surface of the eye. Hennessy A. L. et al. "A Video Study of Drop Instillation in Both Glaucoma and Retina Patients with Visual Impairment." *Am. J. Ophthalmol.* 2011; 152(6):982-98.

Ocular hypertension or elevated IOP occurs when the pressure inside the eye is higher than normal. Eye pressure is usually expressed in millimeters of mercury, (mm Hg) or kPa. Normal eye pressure is generally considered to be between 12-21 mm Hg, this "normal" upper limit may vary in patient populations to 22 mm Hg. In the healthy eye, a clear fluid called aqueous humor circulates inside the front (30, see FIGS. 1A, 1C) portion of the eye. To maintain a constant healthy eye pressure, the eye continually produces a small amount of aqueous humor while an equal amount of this fluid flows out of the eye. The fluid flows out of the eye through a complex network of cells and tissue in an area called the drainage angle. These include the trabecular meshwork and the endothelial cells of Schlemm's canal, which together control pressure dependent aqueous humor outflow (see 22 FIG. 1C). A pressure independent pathway for aqueous humor outflow is located in the anterior portion of the ciliary muscle (see 24 of FIG. 1C). If the aqueous humor does not flow through the chamber angle properly, fluid pressure builds in the eye, causing ocular hypertension or elevated IOP. Ocular hypertension can also result if the eye produces too much aqueous humor. Injury to the eye can also cause ocular hypertension, as can certain eye diseases. Population groups most susceptible to ocular hypertension are patients with a family history of ocular hypertension or glaucoma, patients with diabetes, patients over the age of forty years old, people of African descent and myopic patients.

Ocular hypertension or elevated IOP is not the same as glaucoma. Glaucoma refers to a family of diseases of the eye usually caused by high intraocular pressure. However, a patient may have elevated IOP and not suffer from glaucoma. Glaucoma is generally divided between open angle glaucoma and closed angle glaucoma. Open angle chronic glaucoma is more common, is usually painless, and develops slowly over time and often has no symptoms until the disease has progressed significantly. Open angle glaucoma is usually treated with glaucoma medication to lower the intraocular pressure. Closed-angle glaucoma involves sudden eye pain resulting from a sudden spike in intraocular pressure, and is treated as a medical emergency. Glaucoma can permanently damage vision in the affected eye(s), first by decreasing peripheral vision and then potentially leading to blindness if left untreated.

Elevated intraocular pressure (above 21 mmHg or 2.8 kPa) is the most important and the only modifiable risk factor for glaucoma. The term "low tension" or "normal tension glaucoma" refers to patients with optic nerve damage and associated visual field loss, but normal or low intraocular pressure. Glaucoma has been called the "silent thief of sight" because the loss of vision often occurs gradually over a long period of time, and symptoms often occur only when the disease is quite advanced. Once lost, vision cannot normally be recovered, so treatment is aimed at preventing further loss. Worldwide, glaucoma is the second-leading cause of blindness after cataracts.

Ocular hypertension and glaucoma are usually treated with topical eye drops administered once or twice a day to control elevated IOP. These eye drops usually consist of compounds such as alpha agonists, beta-blockers, cholinergic agents, prostaglandin analogs and combinations of these compounds. While these compounds are effective at lowering IOP, these compounds have the disadvantage of having to be topically applied by self-administration to the front (30, FIGS. 1A and 1C) of the eye once or twice a day. Along with significant patient compliance issues, daily use of such compounds often result in side effects such as surface hyperemia, or redness to the eye, which cause patients to stop using the drugs. The maximum reduction in IOP by drug treatment is typically up to a 30% lowering in elevated IOP.

Ocular implants are another method of lowering elevated IOP. Ocular implants are surgically implanted in the eye and release an IOP lowering drug on a continuous basis for a period of usually three to six months and then the implant must be replaced. The advantages of ocular implants are that once inserted into the eye, the drug is automatically administered. Disadvantages of ocular implants are they are surgically invasive and require replacement every three to six months which amounts to additional surgery. Many patients also have an aversion to injection of ocular implants into their eye and prefer topical drops.

Another class of compounds that has been shown to lower IOP are prostanoid $EP_2$ agonists. While many prostanoid $EP_2$ agonists are effective at lowering IOP in patients with elevated IOP and glaucoma, there are significant side effects associated with $EP_2$ agonists that preclude their use as a daily-administered drug, such as thickening of the corneal epithelium and cellular infiltration into the aqueous humor. These side effects frequently occur when an $EP_2$ agonist is applied topically to the eye every day and on a continuous basis. If these side effect issues could be overcome, the use of an $EP_2$ agonist as an IOP lowering drug would be an attractive alternative to other commercially available compounds.

SUMMARY OF THE INVENTION

The present invention is directed to compounds that are EP2 agonists useful for lowering IOP or treating glaucoma. The EP agonists of the present invention have the following general structure with a difluoro biphenyl moiety:

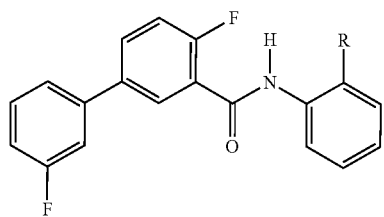

wherein R may be selected from the group consisting of:

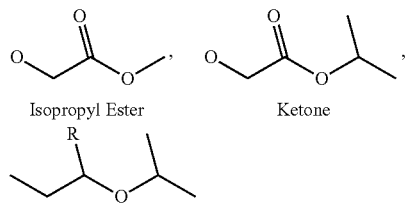

Isopropyl Ester     Ketone

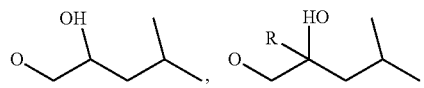

wherein R may be Cl or Br, which may be slightly unstable, CF3, alkyl and H which is very stable;

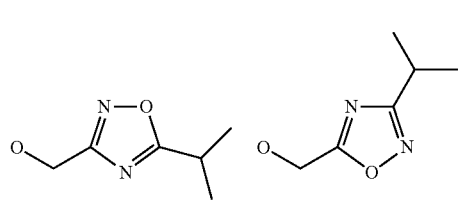

wherein R is methyl, isobutyl,

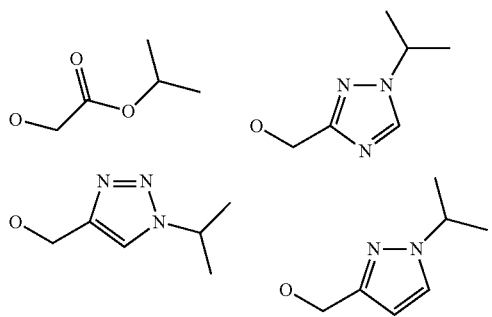

Some compounds of the present invention may include:

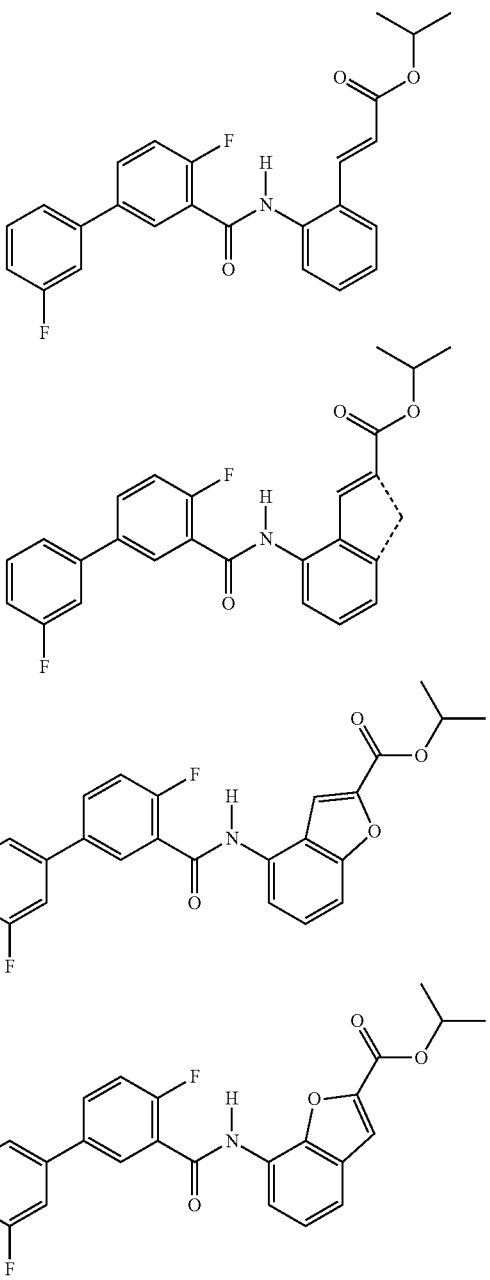

-continued
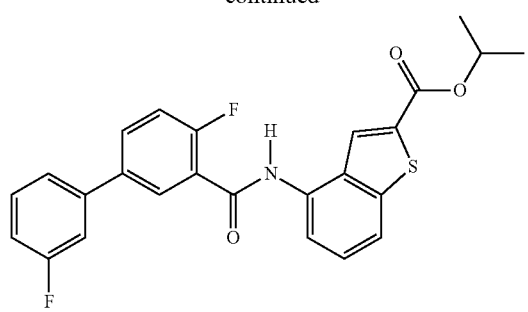
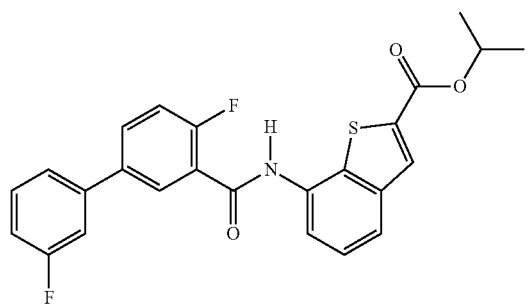
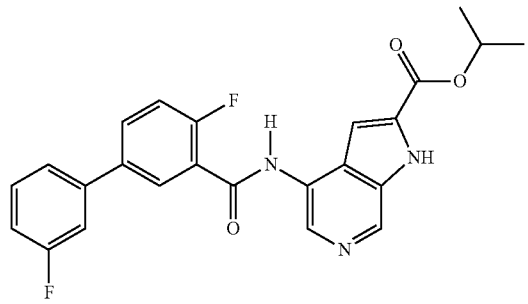
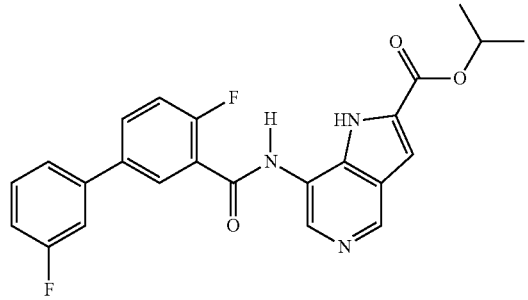
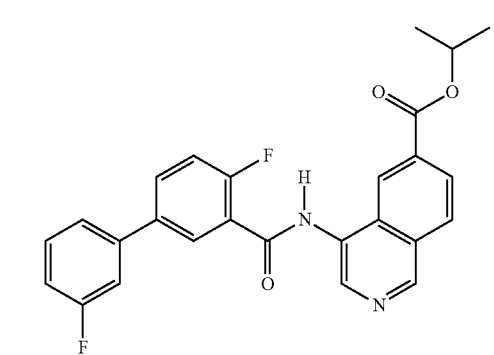
-continued
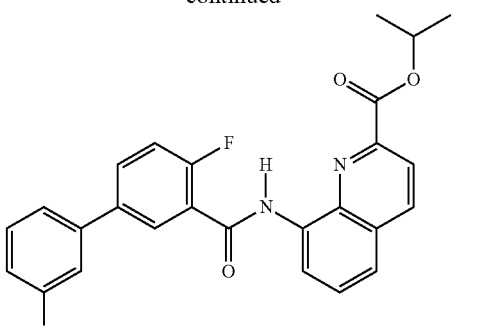
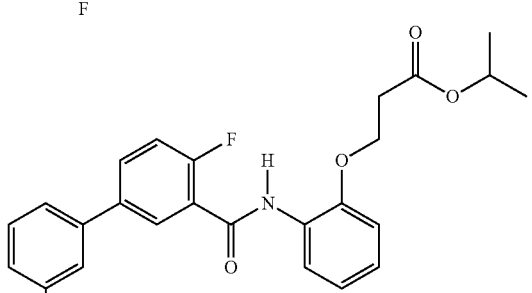
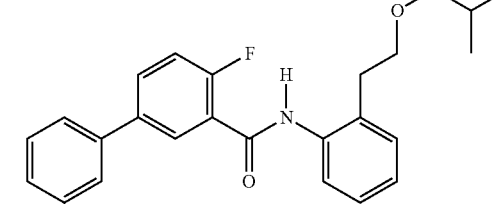
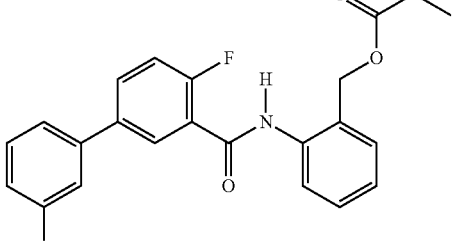
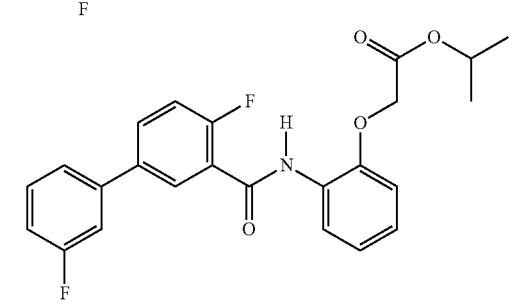
and their salts.
More particularly, the present invention is directed to the following EP$_2$ agonist, its free acid, esters, and salts and its administration to the periorbital skin resulting in long lasting reduction in IOP. The EP2 agonist is 3-[(3'-fluoro-fluorobiphenyl-3-carbonyl) amino] phenoxyacetic acid isopropyl ester:

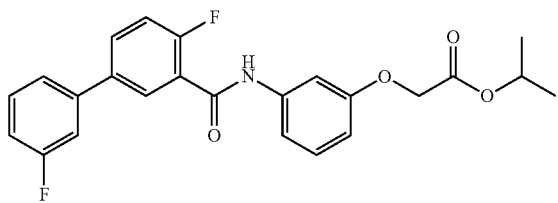 [SMILES: CC(C)OC(=O)COc1cccc(NC(=O)c2cc(-c3cccc(F)c3)ccc2F)c1]

Its free acid is:

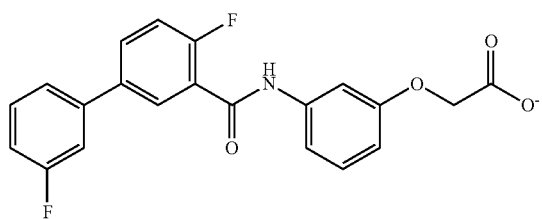 [SMILES: O=C([O-])COc1cccc(NC(=O)c2cc(-c3cccc(F)c3)ccc2F)c1]

Possible salts are:

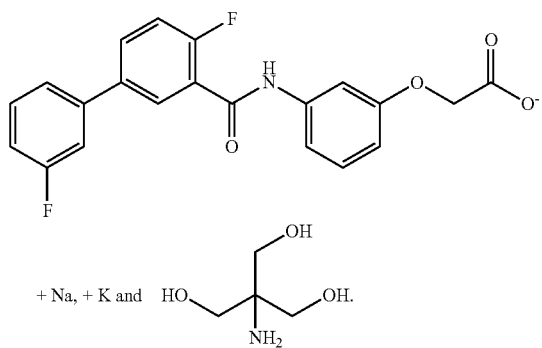
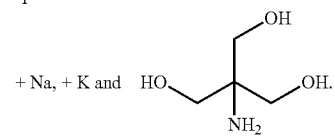

When applied to the eye through the periorbital skin (10, see. FIGS. 1A-1C) of the eye, rather than topically to the surface of the eye (30) or the eyelid (12 or 26) of the eye (see FIGS. 1A-1C), formulations of the above compound have proven to be effective in lowering IOP for up to 7 to 14 days with a single administration and/or after a series of single administrations (up to five daily serial or consecutive administrations and then once a week thereafter). The result is a profound IOP lowering effect, without the unwanted side effects of daily topical application of an IOP lowering agent to the front of the eye (30) and without the side effects seen with topical administration of $EP_2$ agonists such as corneal epithelium thickening, cellular infiltration and hyperemia.

The compound of the present invention, when applied to the periorbital tissue, acts as a super IOP lowering drug with a single dosage lowering IOP for periods of up to and over seven days, thereby allowing once a week administration and not requiring the use of daily or multiple daily applications.

The present invention is also directed to methods of treating ophthalmic diseases by application of drugs over the periorbital tissue of the eye.

The present invention is also directed to various mechanisms of delivering ophthalmic drugs to the periorbital surface of the eye.

Some embodiments of the present invention include but are not limited to:

1) A method of lowering intraocular pressure in a patient suffering from elevated intraocular pressure or glaucoma comprising administering a composition comprising an $EP_2$ agonist to the periorbital skin of each eye of the patient.
2) The method of embodiment 1 wherein the $EP_2$ agonist is 3-[(3'-fluoro-4-fluorobiphenyl-3-carbonyl) amino] phenoxyacetic acid isopropyl ester.
3) The method of embodiments 1 and 2 wherein the composition comprising 3-[(3'-fluoro-4-fluorobiphenyl-3-carbonyl) amino] phenoxyacetic acid isopropyl ester is applied to the periorbital skin of each eye of the patient once every selected from the group consisting of one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine and thirty days to effectively lower intraocular pressure or treat glaucoma.
4) The method of embodiments 1 and 2 wherein the composition comprising 3-[(3'-fluoro-4-fluorobiphenyl-3-carbonyl) amino] phenoxyacetic acid isopropyl ester is in the form of one selected from the group consisting of a solution, an emulsion, a suspension, and a dispersion and is applied topically to the periorbital skin of the eye by a device which administers the composition in specifically dosed amounts over the periorbital skin of the patient.
5) The method of embodiment 4 wherein the device traces an area over the periorbital skin selected from the group consisting of at least once, twice or three times in order to deliver the drug.
6) The method of embodiments 1 and 2 wherein the composition is in the form of one selected from the group consisting of a topical cream, gel, hydrogel, organogel, xerogels, lotion, nanocomposite hydrogels, foam, and a solution in an organic solvent.
7) The method of embodiment 6 wherein the composition is applied over the upper and lower periorbital skin of each eye and is not applied to the upper or lower eyelid or eyelid margin.
8) The method of embodiment 6 wherein the composition is applied over the upper and lower periorbital skin of each eye before sleeping.
9) The method of embodiment 4 wherein the composition comprising 3-[(3'-fluoro-4-fluorobiphenyl-3-carbonyl) amino] phenoxyacetic acid isopropyl ester is a solution or an emulsion.
10) The method of embodiments 1 and 2 wherein the composition comprising 3-[(3'-fluoro-4-fluorobiphenyl-3-carbonyl) amino] phenoxyacetic acid isopropyl ester is applied to the periorbital skin for up to five consecutive days and thereafter once a week and the composition lowers elevated intraocular pressure to normal levels for up to one week between dosings.
11) The method of embodiments 1 and 2 wherein the composition comprising 3-[(3'-fluoro-4-fluorobiphenyl-3-carbonyl) amino] phenoxyacetic acid isopropyl ester is applied once and lowers elevated intraocular pressure for up to between seven to fourteen days with a single administration.

12) The method of embodiment 2 wherein the composition comprising 3-[(3'-fluoro-4-fluorobiphenyl-3-carbonyl) amino] phenoxyacetic acid isopropyl ester is applied to the periorbital skin of the upper eyelid.
13) The method of embodiment 2 wherein the composition comprising 3-[(3'-fluoro-4-fluorobiphenyl-3-carbonyl) amino] phenoxyacetic acid isopropyl ester is applied to the periorbital skin of the upper and lower eyelid.
14) The method of embodiment 4 wherein the composition is administered from a device which releases a preselected dosage in an approximate uniform manner on the periorbital skin.
15) The method of embodiment 14 wherein the composition is delivered in an elliptical line that traces the periorbital skin.
16) The method of embodiments 1 and 2 wherein the composition is dosed once every 5, 6 or 7 days and as a result the patient's IOP is maintained between 12-22 or 12-21 mmHg.
17) The method of embodiments 1 and 2 where the composition is dosed once every 5 days and as a result the patient's IOP is maintained between 12-22 or 12-21 mm Hg.
18) The method of embodiments 1 and 2 where the composition is dosed once every 6 days and as a result the patient's IOP is maintained between 12-22 or 12-21 mm Hg.
19) The method of embodiments 1 and 2 where the composition is dosed once every 7 days and as a result the patient's IOP is maintained between 12-22 or 12-21 mm Hg.
20) The method of embodiments 1 and 2 wherein the $EP_1$ agonist is present in the composition with the following concentrations selected from the group consisting of 0.01%, 0.02%, 0.03%, 0.04%, 0.05%, 0.06%, 0.07%, 0.08%, 0.09%, 0.10%, 0.2%, 0.3%, 0.4%, 0.5%, 0.6%, 0.7%, 0.8%, 0.9%, 1%, 2%, 3%, 4%, 5%, 6%, 7%, 8%, 9%, and 10% w/v or w/w.
21) The method of embodiments 1 and 2 wherein the composition has fewer side effects than the same composition applied directly to the front of the eye by topical administration at the same dosage and frequency of administration.
22) The method of embodiments 1 or 2 wherein the composition is useful for treating elevated IOP.
23) The method of embodiments 1 or 2 wherein the composition is useful for treating glaucoma.
24) The method of embodiments 1 or 2 wherein the composition results in significantly less hyperemia than the same composition applied topically to the front of the eye by topical administration at the same dosage and frequency of administration.
25) The method of embodiments 1 and 2 wherein the composition results in less corneal thickening than the same composition applied topically to the front of the eye by topical administration at the same dosage and frequency of administration.
26) The method of embodiments 1 and 2 wherein the composition is applied to the upper and lower periorbital skin at least once for a single administration.
27) The method of embodiments 1 and 2 wherein the composition is applied to the upper and lower periorbital skin of the eye at least twice for a single administration.
28) The method of embodiments 1 and 2 wherein the composition is applied to the upper and lower periorbital skin of the eye at least three times for a single administration.
29) The method of embodiments 1 and 2 wherein the composition is applied to the upper and lower periorbital skin of the eye at least four times for a single administration.
30) The method of embodiments 1 and 2 wherein the composition is applied to the upper and lower periorbital skin of the eye five times for a single administration.
31) 3-[(3'-fluoro-4-fluorobiphenyl-3-carbonyl) amino] phenoxyacetic acid isopropyl ester for the treatment of elevated IOP or glaucoma comprising the step of administering 3-[(3'-fluoro-4-fluorobiphenyl-3-carbonyl) amino] phenoxyacetic acid isopropyl ester to the periorbital skin above and below the eyelids of each eye once selected from the group of every five, six or seven days.
32) The use of 3-[(3'-fluoro-4-fluorobiphenyl-3-carbonyl) amino] phenoxyacetic acid isopropyl ester for the manufacture of a medicament for treating elevated IOP or glaucoma, wherein the medicament is prepared to be administered selected from the group consisting of once every five, six or seven days to the periorbital skin above and below the eyelids of an eye to maintain IOP at normal levels.
33) The uses of embodiments 31 or 32 wherein the IOP of the patient is maintained at normal levels between dosings.
34) Embodiments 31, 32 or 33 wherein 3-[(3'-fluoro-4-fluorobiphenyl-3-carbonyl) amino] phenoxyacetic acid isopropyl ester is in a composition selected from the group consisting of a solution, a suspension, a dispersion, emulsion, cream, gel, hydrogel, organogel, xerogels, lotion, nanocomposite hydrogels, foam, and a solution in an organic solvent.
35) Use of 3-[(3'-fluoro-4-fluorobiphenyl-3-carbonyl) amino] phenoxyacetic acid isopropyl ester for the manufacture of a medicament for the treatment of elevated IOP or glaucoma wherein the medicament is applied to the periorbital skin of each eye at least once selected from the group consisting of every one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine and thirty days and results in lowering IOP to normal levels.
36) A method of ophthalmic drug delivery and achieving therapeutic effects at the ocular surface and anterior segment tissues by periorbital administration of a drug.
37) A method of treating ocular diseases by applying drug by one selected from the group consisting of a roller/reservoir device, brush, or applicator to the periorbital skin that surrounds the eye socket.
38) The method of embodiments 36 and 37 wherein the drug is intended to treat dry eye.
39) The method of embodiment 38 wherein the drug is cyclosporine.
40) The method of embodiment 38 wherein the drug is selected from the group consisting or cyclosporine, its isoforms, analogs, and derivatives including prodrugs.
41) The method of embodiments 36 and 37 wherein the drug is intended to treat eye allergies.

42) The method of embodiments 36 and 37 wherein the drug is intended to treat infectious conjunctivitis.
43) The method of embodiments 36 and 37 where the drug is intended to treat at least one selected from the group consisting of ocular discomfort, pain, itch and related sensory modalities.
44) The method of embodiments 36 and 37 wherein the drug is a surgical adjunct.
45) The method of embodiments 36 and 37 wherein the drug is intended to treat "puffy" eyes by reducing fat deposition and/or fluid accumulation in the periorbital region of the eye. The appearance of "puffy" may also be treated by restoration of connective tissue.
46) The method of embodiments 36 and 37 wherein the drug has anti-inflammatory and/or immunosuppressive properties.
47) The method of embodiment 6 wherein the vehicle is an organic hydrophobic entity, a cream, an emulsion, or is aqueous based and containing sufficient drug compound to exert the desired effect.
48) The method of embodiment 6 wherein the formulation contains a penetration enhancer selected from the group consisting of oleyl alcohol, Transcutol® and polyethylene glycol.
49) A roller/reservoir device where the reservoir is graduated to monitor and deliver a specific drug/composition delivery quantity to the periorbital skin.
50) The device of embodiment 49 wherein the drug composition is contained in a reservoir fitted with a rotating or vertical ratchet to provide measured dose delivery to the periorbital skin.
51) The device of embodiments 49 and 50 wherein the periorbital skin delivery device interface is by means of a fiber tip, felt tip, or specialized brushing device adapted to fit the reservoir design of choice.
52) A method of topical delivery to the periorbital skin that allows formulations containing 100% organic solvent to be used with or without preservative.
53) A method of topical delivery to the periorbital skin for the treatment of ocular diseases without the burning/stinging sensations, photophobia, and other unwanted side effects associated with drops administered directly to the eyeball.
54) The method of embodiments 36 and 37 wherein the drug is an eicosanoid.
55) The method of embodiments 1 and 36 wherein the drug is a prostanoid $EP_2$ receptor agonist.
56) The method of embodiment 36 wherein the drug is a lacrimal gland stimulant/secretogogue.
57) The method of embodiments 36 and 37 wherein the drug is an immunomodulating agent.
58) The method of embodiments 36 and 37 wherein the drug is a glucocorticoid.
59) The method of embodiments 36 and 37 wherein the drug is an anti-histamine.
60) The method of embodiments 36 and 37 wherein the drug is an adrenergic agent.
61) The method of embodiments 36 and 37 wherein the drug is a mast cell stabilizer.
62) The method of embodiments 36 and 37 wherein the drug is an antibiotic.
63) The method of embodiments 36 and 37 wherein the drug is an antiviral.
64) The method of embodiments 36 and 37 wherein the drug is a non-steroidal anti-inflammatory agent or a prostanoid $EP_2$ receptor agonist.
65) The method of embodiments 36 and 37 wherein the drug is a prostaglandin receptor antagonist.
66) The method of embodiments 36 and 37 wherein the drug is a prostanoid or a prostamide.
67) The method of embodiments 36 and 37 wherein the drug is an antineoplastic agent.
68) The method of embodiments 36 and 37 wherein ocular surface and anterior chamber side effects are reduced.
69) The method of embodiments 36, 37 and 59 wherein the drug is an anti-allergy drug and is selected from the group consisting of alcaftadine, cromolyn, dexamethasone, difluprednate, fluorometholone, loteprednol, rimexolone, azelastine, epinastine, ernedastine difurnarate, olopatadine, cromolyn ophthalmic, lodoxamide, nedocromil, bromfenac, diclofenac, flurbiprofen, ketorolac, nepafenac, loradatine, hydroxyzine, diphenhydramine, chlorpheniramine, azelastine hydrochloride brompheniramine, cyproheptadine, terfenadine, clemastine, levocabastine, triprolidine, carbinoxamine, diphenylpyraline, phenindamine, azatadine, tripelennamine, dexchlorpheniramine, dexbrompheniramine, methdilazine, and trimprazine doxylamine, pheniramine, pyrilamine, pemirolast, chiorcyclizine, thonzylamine and/or mixtures of at least two thereof.
70) The method of embodiments 36, 37 and 67 wherein the drug is an antineoplastic agent and is selected from the group consisting of cisplatin, etoposide, interferons, camptothecin and derivatives thereof, phenesterine, taxol and derivatives thereof, taxotere and derivatives thereof, vinblastine, vincristine, tamoxifen, etoposide, piposulfan, cyclophosphamide, flutamide, adriamycin, cyclophosphamide, actinomycin, bleomycin, duanorubicin, doxorubicin, epirubicin, mitomycin, methotrexate, fluorouracil, carboplatin, carmustine (BCNU), and methyl-CCNU and/or mixtures of at least two thereof.
71) The method of embodiments 36, 37 and 62 wherein the drug is an antibiotic and is selected from the group consisting of ampicillin, amoxicillin, cyclacillin, ampicillin, cefazolin, cephradine, cefaclor, cephapirin, ceftizoxime, cefoperazone, cefotetan, cefutoxime, cefotaxime, cefadroxil, ceftazidime, cephalexin, cephalothing cefamandole, cefoxitin, cefonicid, ceforanide, ceftriaxone, cefadroxil, cephradine, cefuroxime, cyclosporine, gentamicin, tobramycin, besifloxacin, ciprofloxacin, gatifloxacin, levofloxacin, moxifloxacin, ofloxacin, azithromycin, erythromycin, bacitracin, bacitracin/polymyxin, natamycin, neomycin/polymyxin B/bacitracin, neomycin/polymyxin B/gramicidin, polymyxin B/trimethoprim, penicillin G, penicillin V potassium, piperacillin, oxacillin, bacampicillin, cloxacillin, ticarcillin, azlocillin, carbenicillin, methicillin, nafcillin, erythromycin, tetracycline, doxycycline, minocycline, aztreonam, chloramphenicol, ciprofloxacin hydrochloride, clindamycin, metronidazole, gentamicin, lincomycin, tobramycin, vancomycin, polymyxin B sulfate, colistimethate, colistin, azithromycin, augmentin, sulfamethoxazole, and trimethoprim and/or mixtures of at least two thereof.
72) The method of embodiments 36 and 37 wherein the drug is a β-adrenergic receptor blocker and is selected from the group consisting of acebutolol, atenolol, labetalol, metoprolol, propranolol, timolol maleate and/or mixtures of at least two thereof.
73) The method of embodiments 36 and 37 wherein the drug is an anti-inflammatory agent, including steroids, NSAIDs (non-Steroidal Anti-Inflammatory Drugs), COX inhibitors, or prostanoid receptor inhibitors blocking single or multiple receptors. Corticoands, such as cortisone, prednisolone, fluorometholone, dexamethasone, medrysone, loteprednol fluazacort, hydrocortisone, prednisone, betamethasone, methylprednisolone, riamcinolone hexacatonide, paramethasone acetate, diflorasone, fluocinonide, fluocinolone, and triamcinolone; non-steroidal anti-inflammatory agents, such as aspirin, diclofenac, rofecoxib, ibuprofen, indomethacin; PG antagonists and/or mixtures of at least two thereof.

74) The method of embodiments 36, 37 and 57 wherein the immunomodulating agent is selected from the group consisting of cyclosporine, azathioprine, methotrexate, and tacrolimus and/or mixtures of at least two thereof.

75) The method of embodiments 36, 37 and 63 wherein the antiviral agent is selected from the group consisting of interferon gamma, zidovudine, amantadine hydrochloride, ribavirin, acyclovir, valciclovir, dideoxycytidine, phosphonoformic acid, ganciclovir and/or mixtures of at least two thereof.

76) The method of embodiments 36 and 37 wherein the drug is selected from the group consisting of phentolamine, testosterone, dexamethasone, bimatoprost, latanoprost, travoprost, tafluprost, pilocarpine, brimonidine tartrate and/or mixtures of at least two thereof.

77) The method of embodiments 36 and 37 wherein the patient is suffering from a disease or condition selected from the group consisting of age related macular degeneration, allergies, amblyopia, aniscoria, astigmatism, bacterial keratitis, blepharitis, branch retinal vein occlusion, cataracts, chalazia, chordial neovascular membrane growth, conjunctivitis, corneal abrasion, corneal laceration, corneal ulcer, cytomegalovirus retinitis, diabetic retinopathy, drusen, dry eye, eye cancer, eye lymphoma, farsightedness, Fuchs' dystrophy, fungal keratitis, glaucoma, Gravis disease, herpes keratitis, histoplasmosis/ocular histoplasmosis syndrome, HIV/AIDS, hyplema iridocorneal syndrome, ischemic optic neuropathy, juvenile macular degeneration, keratitis, kertaconus, low vision, macular edema, macular hole, macular telangiectasia, microvascular cranial nerve palsy, night blindness or poor night vision, myasthenia gravis, nevus, nystagmus, ocular melanoma, optic neuritis, ocular pain, photokeratitis, pigment dispersion syndrome, pinguecula, presbyopia, ptosis, retinitis pigmentosa, retinoblastoma, retinopathy of premturitis, scleritis, shingles, Stargart disease, strabismus, subjunctival hemorrhage, torn retina, trachoma trichosis, Usher syndrome, uveitis, and vitamin A deficiency.

78) A method of lowering intraocular pressure in a patient suffering from elevated intraocular pressure or glaucoma comprising administering a topical composition comprising 3-[(3'-fluoro-4-fluorobiphenyl-3-carbonyl) amino] phenoxyacetic acid isopropyl ester to the front of the eye of the patient by a topical drop or to the back of the eye in an ocular implant.

79) A method of treating puffy eye or periorbital puffiness by administering hyaluronic acid, aloe vera, vitamin C and retinol to the periorbital skin. In addition a method of treating puffy eye by administering a sympathomimetic agent such as Sympathomkimetics phen ytpropanolamine, ephedrine, methoxyphenamine, yohimbine, tyrosine, dopamine, caffeine, theobromine, papaverine, tranylcypromine, amitriptyline, iprindoie, theophylline, amphetamine, pseudoephedrine, norpseudoephedrine, diethytpropion, benzphetamine, phendimetrazine, phenmetrazine, phenterraine, chorphentermine, arninorex; administering an α-adrenergic agonists such norepinephrine, clonidine, dexmetdetomidine, apractonidine, tizanidine, brimonidine, xylometazoline, tetrahydrozotine, oxymetazoline, guanfacine, guanabenz, xylazine, moxonidine, ramenidine, B-HT 933, BHT administering a β-adrenergic agonist such as epinephrine, bambuterol, bitolteroi, broxaterot, carbuterol, carmoterot, cienbuterol, ibuterol, sulfonterol, isoproterenol, trimetoquinot, formoterol, desformoterot, hexoprenaline, ibuterol, indacaterol, isoetharine, isoprenaline, isoproterenol, levalbuterol metaproterenol pieumeterol pirbuterol, procaterol, reproterol, rimiterol, salbutarnol, salrneterol, sulfonterol, terbutaline, tritnetoquinol, tulobuterol, TA-2005 (8-hydroxy-5-((1R)-1-hydroxy-2-(N-((1R)-2-(4-methoxyphenyl)-1-methylethyl-)amino)ethyl)-carbostyril hydrochloride, QAB-1.49 (Novartis), TA 2005, GSK-159797, or GSK-642444, L BHT920, mivazerol, octopamine, tizanidine.

80) A method of treating periorbital lines comprising administering α-adrenergics such as norepinephrine and brimonidine and β-adrenergics such as epinephrine, norepinephrine, salbutamol, and salmeterol and hyaluronic acid, aloe vera, vitamin C and retinol to the periorbital skin.

DETAILED DESCRIPTION OF THE INVENTION

Figure 1C:
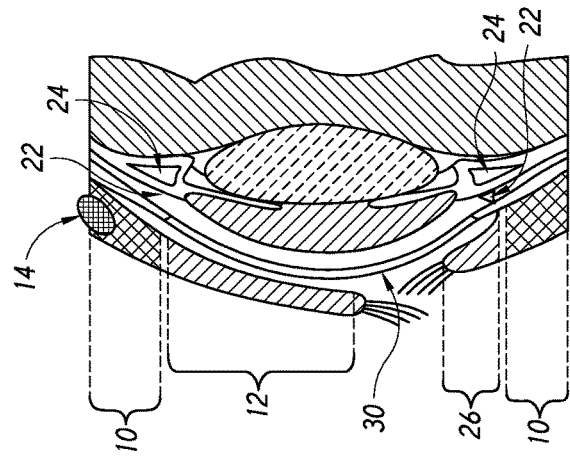
FIGS. 1A-1C show the site of periorbital administration of drugs to the human eye; and, FIG. 2 shows long term IOP lowering after five doses of 3-[(3'-fluoro-4-fluorobiphenyl-3-carbonyl) amino] phenoxyacetic acid isopropyl ester.

The terms "about", "approximate" and "approximately" are used herein to modify a numerical value and indicate a defined range around that value. If "X" were the value, "about X" or "approximately equal to X" would generally indicate a value from 0.90X to 1.10X. Any reference to "about X" minimally indicates at least the values X, 0.90X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, and 1.10X. Thus, "about X" is intended to disclose, e.g., "0.98X." When "about" is applied to the beginning of a numerical range, it applies to both ends of the range. Thus, "from about 6 to 8.5" is equivalent to "from about 6 to about 8.5." When "about" is applied to the first value of a set of values, it applies to all values in that set. Thus, "about 7, 9, or 11%" is equivalent to "about 7%, about 9%, or about 11%." About may also refer to a number close to the cited number that would result in a bioequivalent therapeutic effect by a regulatory agency such as the FDA or the EMEA.

The terms "active", "active agent", "active pharmaceutical ingredient", "API" and "drug" refer to the active ingredient of a composition. An API is typically a chemical substance or mixture of chemical substances. Such substances are intended to furnish pharmacological activity or other direct effect in the diagnosis, cure, mitigation, treatment or prevention of disease of the eye.

The term "daily" means every day and may refer to once a day or multiple times a day such as BID or TID dosing.

The terms "effective amount," "therapeutically effective amount" or "pharmaceutically effective amount" refer to an amount of an active agent effective to treat elevated IOP or glaucoma or other ophthalmic diseases, including a range of effects, from a detectable amount of improvement to substantial relief/improvement of symptoms or a cure of the disease or condition. The result can be reduction and/or alleviation of the signs, symptoms, or causes of a disease, or any other desired alteration of a biological system. For example, an "effective amount" for therapeutic uses is the amount of the composition comprising an agent as set forth herein required to provide a clinically significant decrease in an ophthalmic disease. For example, for the given aspect (e.g., length of incidence), a therapeutically effective amount will show an increase or decrease of at least 5%, 10%, 15%, 20%, 25%, 40%, 50%, 60%, 75%, 80%, 90%, or 100%. Therapeutic efficacy can also be expressed as "-fold" increase or decrease. For example, a therapeutically effective amount can have at least a 1.2-fold, 1.5-fold, 2-fold, 5-fold, or more effect over a control. An appropriate "effective" amount in any individual case may be determined using techniques, such as a dose escalation study.

"Elevated intraocular pressure" shall mean intraocular pressure above 21-22 mm Hg.

"Emulsion" means, but is not limited to, an oil-in-water emulsion, a water-in-oil emulsion, a micro emulsion referring to particle sizes of $10^{-9}$.

"$EP_2$ agonist" shall refer to an agonist of the prostaglandin E2 receptor.

"Formulation" and "composition," are intended to be equivalent and refer to a composition of matter suitable for pharmaceutical use (i.e., producing a therapeutic effect as well as possessing acceptable pharmacokinetic and toxicological properties).

Figure 1B:
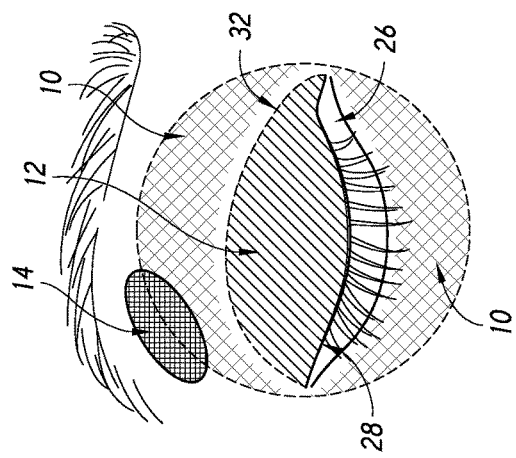
Figure 1A:
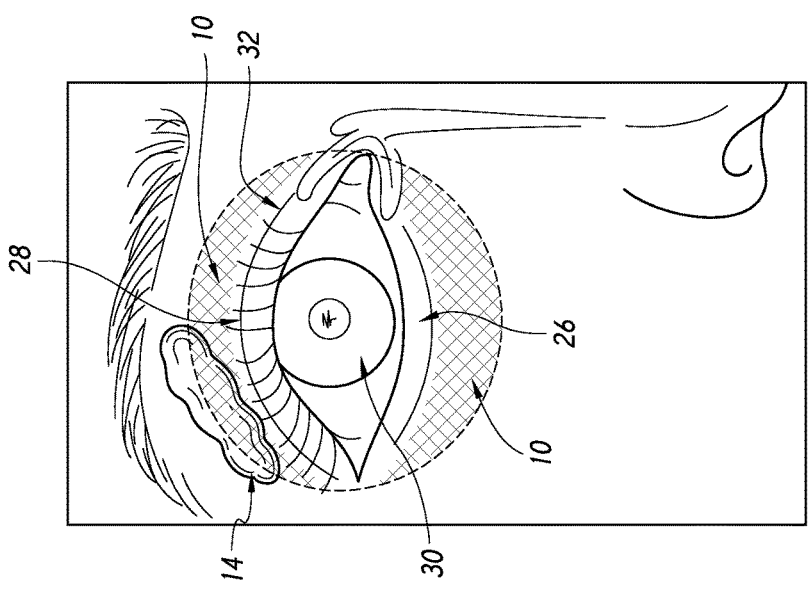

"Periorbital administration" involves administration to the periorbital skin (10) as shown in FIGS. 1A-1C and specifically excludes administration to the upper eyelid (12), lower eyelid (26) and eyelid margin (28).

"Pharmaceutically acceptable" is used as equivalent to physiologically acceptable. In certain embodiments, a pharmaceutically acceptable composition or preparation will include agents for buffering and preservation in storage, and can include buffers and carriers for appropriate delivery, depending on the route of administration.

"Preselected dosage" shall mean a dosage selected prior to administration.

As used herein, the terms "prevent" and "treat" are not intended to be absolute terms. Treatment can refer to any delay in onset, e.g., reduction in the frequency of or severity of symptoms, amelioration of symptoms, improvement in patient comfort, reduction in IOP, treatment of glaucoma, and the like. The effect of treatment can be compared to an individual or pool of individuals not receiving a given treatment, or to the same patient before, or after cessation of, treatment.

The terms "subject," "patient," "individual," are not intended to be limiting and can be generally interchanged. That is, an individual described as a "patient" does not necessarily have a given disease, but may be merely seeking medical advice. The term "subject" as used herein includes all members of the animal kingdom prone to suffering from the indicated disorder. In some aspects, the subject is a mammal, and in some aspects, the subject is a human.

"Treating" or "treatment" as used herein includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, delay or slowing of disease progression, amelioration, diminishment of the reoccurrence of disease. Treatment may prevent the disease from occurring; relieve the disease's symptoms, fully or partially remove the disease's underlying cause, shorten a disease's duration, or do a combination of the above.

"Treating" and "treatment" as used herein may also include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for duration sufficient to treat the patient.

As used herein, "topical", "topical application," "topical administration," and "topically administering" are used interchangeably herein and include the administration to the front of the eye of a subject. Topical application or administering may result in the delivery of an active agent to the eye.

"Topical formulation" and "topical pharmaceutical composition" are used interchangeably herein and include a formulation that is suitable for topical application to the eye. A topical formulation may, for example, be used to confer a therapeutic benefit to its user.

As used herein, the phrase "pharmaceutically acceptable salts" refers to salts of the active compound(s) which possess the same pharmacological activity as the active compound(s) and which are neither biologically nor otherwise undesirable. A salt can be formed with, for example, organic or inorganic acids. Non-limiting examples of suitable acids include acetic acid, acetylsalicylic acid, adipic acid, alginic acid, ascorbic acid, aspartic acid, benzoic acid, benzenesulfonic acid, bisulfic acid, boric acid, butyric acid, camphoric acid, camphorsulfonic acid, carbonic acid, citric acid, cyclopentanepropionic acid, digluconic acid, dodecylsulfic acid, ethanesulfonic acid, formic acid, fumaric acid, glyceric acid, glycerophosphoric acid, glycine, glucoheptanoic acid, gluconic acid, glutamic acid, glutaric acid, glycolic acid, hemisulfic acid, heptanoic acid, hexanoic acid, hippuric acid, hydrobromic acid, hydrochloric acid, hydroiodic acid, hydroxyethanesulfonic acid, lactic acid, maleic acid, malic acid, malonic acid, mandelic acid, methanesulfonic acid, mucic acid, naphthylanesulfonic acid, naphthylic acid, nicotinic acid, nitrous acid, oxalic acid, pelargonic, phosphoric acid, propionic acid, saccharin, salicylic acid, sorbic acid, succinic acid, sulfuric acid, tartaric acid, thiocyanic acid, thioglycolic acid, thiosulfuric acid, tosylic acid, undecylenic acid, naturally and synthetically derived amino acids.

Non-limiting examples of base salts include ammonium salts; alkali metal salts, such as sodium and potassium salts;

alkaline earth metal salts, such as calcium and magnesium salts; salts with organic bases, such as dicyclohexylamine salts; methyl-D-glucamine; and salts with amino acids, such as arginine, lysine, and so forth. Also, the basic nitrogen-containing groups can be quaternized with such agents as lower alkyl halides, such as methyl, ethyl, propyl, and butyl chlorides, bromides, and iodides; dialkyl sulfates, such as dimethyl, diethyl, dibutyl, and diamyl sulfates; long chain halides, such as decyl, lauryl, myristyl, and stearyl chlorides, bromides, and iodides; asthma halides, such as benzyl and phenethyl bromides; and others.

The compositions can be administered prior to, concurrently with, and/or after the development of elevated IOP or glaucoma or any other eye disease or condition. The compositions may be administered between once and twice a week, for a period of time necessary to achieve the desired results, which may be several days to several months or continuously. The compositions can be administered once or several times (2, 3, 4, or more times) a day depending on the desired effect. In certain embodiments, the compositions can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30 days. In another embodiment, the compositions can be administered one or more times every 1, 2, 3, or 4 weeks. The administration can be on a monthly or bi-monthly basis. Further, the compositions can be administered for 1, 2, 3, 6, 9, or 12 months or continuously. In certain embodiments, the compositions can be administered on an ongoing basis to maintain a desired result. The compositions can be administered once a day, twice a day, three times a day and up to four times a day.

As used herein, "carrier," "acceptable carrier" and "vehicle" may be used interchangeably and refer to a carrier which may be combined with the presently disclosed compounds in order to provide a desired composition. In accordance with one embodiment, the composition includes an ophthamologically acceptable vehicle or carrier. The vehicle, which may be employed for preparing compositions may comprise, for example, aqueous solutions, dispersions, emulsions, suspensions, or ointments.

In accordance with the disclosure, the ophthalmic composition of the present invention can optionally include one or more agents such as, without limitation, emulsifying agents, wetting agents, tonicity adjusters, preservatives, buffers antioxidants and flavonoids. Tonicity adjustors useful in a pharmaceutical composition of the present disclosure include, but are not limited to, salts such as sodium acetate, sodium chloride, potassium chloride, mannitol or glycerin and other pharmaceutically acceptable tonicity adjusters. Preservatives useful in the pharmaceutical compositions described herein include, without limitation, benzalkonium chloride, chlorobutanol, thimerosal, phenyl mercuric acetate, Purite® and phenyl mercuric nitrate. Various buffers and means for adjusting pH can be used to prepare a pharmaceutical composition, including but not limited to, acetate buffers, citrate buffers, phosphate buffers and borate buffers. Similarly, antioxidants useful in pharmaceutical compositions are well known in the art and include for example, sodium metabisulfite, sodium thiosulfate, acetyl-cysteine, butylated hydroxyanisole and butylated hydroxytoluene. Flavonoids are compounds found in plants that are well known to have diverse beneficial biochemical and antioxidant effects. Subcategories of flavonoids include: flavones, flavonols, flavanonse and flavanonols. Examples of flavonoids include: luteolin, apigenin, tangeritin, quercetin, kaempferol, myricetin, fisetin, isorhamnetin, pachypodol, rhamnazin, hesperetin, naringenin, eriodictyol, homoeriodictyol, taxifolin, dihydroquercetin, dihydrokaempferol, tannic acid, tannis, condensed tannis, and hydrolysable tannis.

The compounds and compositions described herein may be administered at least in the minimum dose necessary to achieve the desired therapeutic effect. Generally, such doses may be in the range of 50-100 µl/day or per dosing or about 0.005 mg/day to about 1 mg/day. In another example embodiment, the compound or active agents may be present in a composition or formulation in a range of about 50-1000 µl/week or 0.005-10 mg/week. However, the actual amount of the compound to be administered in any given case will be determined by a physician taking into account the relevant circumstances, such as the age and weight of a patient, patient's general physical condition, severity of the elevated IOP, glaucoma or other eye condition or disease. In some instances, dosing is evaluated on a case-by-case basis.

For achieving convenient delivery to the periorbital skin surface, a roller/reservoir device may be used for dispensing a drug composition. Instead of tilting the head back, forcing the eye open, and then squeezing a bottle to get drops onto the ocular surface, roller application has many simplistic advantages. Application by roller allows simple contact with the periorbital skin. The eyes should be kept closed, this provides added convenience for the patient: no forcing the eyes open, no reflex closing on instillation of the drug solution. No unwanted nociceptive sensations from the cornea or conjunctiva would occur. By ratchet devices/mechanisms on the reservoir containing the drug formulation, measured doses may be administered. This is advantageously accurate compared to "drops in the eye", where awkward self-administration, run-off, eye closure on contact are all common issues. Alternative to a roller ball or cylindrical device, periorbital skin contact may also be achieved by fiber tip, felt tip, and brushing devices.

The use of preservatives in eye medications is unwanted by many patients. Eye-drop solutions are aqueous and typically contain a preservative. For application by roller/reservoir device, an aqueous solution or suspension is not required. The solubilizing substance may be selected from either aqueous, part aqueous, or one hundred percent organic solvent based. In the case of one hundred percent organic drug solutions, an anti-infective preservative may not be required. Application of drug substances and the inherent advantages in applying them to periorbital skin have remained unappreciated. Periorbital drug application as an effective way of reducing intraocular pressure and thereby treating glaucoma is particularly surprising, while eye-drops have been used for treating glaucoma and other ocular diseases for more than a century. Drug delivery to the periorbital skin also allows a wide range of solubilizing agents and excipients to be used, and at concentrations that would be unacceptable for direct application to the ocular surface. In short, application to the periorbital skin allows a much wider repertoire of drug solvents and carriers to be used.

The pH of the disclosed compositions can be about 3 to about 8.0, or about 6.5 to about 7.5. In certain embodiments, the pH of the formulation is about 7.0 to about 7.4 or about 7.1 to about 7.3.

Additionally, compositions may be designed to delay release of the compound over a given period of time, or to carefully control the amount of compound released at a given time during the course of treatment.

Table I lists possible aqueous vehicle formulations in the form of solutions of 3-[(3'-fluoro-4-fluorobiphenyl-3-carbonyl) amino] phenoxyacetic acid isopropyl ester but it is intended that any drug referenced in the specification may be included ("Active Agent"):

1-Octyl-2-pyrrolidinone; 1-Decyl-2-pyrrolidinone; and 1-Dodecyl-2-pyrrolidinone;

TABLE I

| Ingredient % | Aqueous Vehicle Formulations | | | | | | | | | | |
|---|---|---|---|---|---|---|---|---|---|---|---|
| w/v | 1 | 2 | 3 | 4 | 5 | 6 | 7 | 8 | 9 | 10 | 11 |
| Active agent | 0.01 | 0.02 | 0.03 | 0.05 | 0.1 | 0.15 | 0.2 | 0.3 | 0.35 | 0.5 | 0.3 |
| NaCl | 0.1 | 0.2 | 0.15 | 0.2 | 0.1 | 0.15 | — | 0.1 | 0.2 | 0.3 | 0.2 |
| EDTA | 0.01 | 0.02 | 0.015 | 0.01 | 0.02 | 0.015 | 0.03 | — | 0.01 | — | 0.02 |
| Mannitol | 1.0 | — | 2.0 | 2.5 | — | 1.0 | 2.0 | — | 5.0 | 2.0 | 3.0 |
| Glycerin | 10.0 | — | 4.0 | 5.0 | 10 | 5 | 10 | — | 5 | 10 | — |
| BAK | 0.15 | 0.2 | 0.1 | 0.2 | — | 0.1 | 0.2 | 0.1 | 0.2 | — | 0.2 |
| Castor Oil | 0.25 | — | 0.2 | 0.5 | — | 1.0 | 0.5 | 0.1 | 1.0 | — | 1.0 |
| Polysorbate 40 | — | 0.1 | — | — | — | 0.3 | — | — | — | — | — |
| Oleyl Alcohol | 0.1 | — | — | 0.5 | — | 0.2 | — | — | 0.1 | 0.1 | — |
| Transcutol ® | 0.05 | 0.2 | — | — | 0.1 | — | 0.05 | — | 0.05 | — | 0.2 |
| Ethanol | 1% | — | 1.5% | 2.0% | 1.0% | — | — | 0.5% | 2.0% | 1.0% | — |
| Boric Acid | — | 1.5% | 1.6% | — | 1.9% | 1.7% | — | — | 1.8% | — | 1.5% |
| Propylene Glycol | — | — | 0.2 | — | 0.1 | 0.01 | 0.1 | 0.1 | — | — | — |
| Carboxymethyl cellulose | — | 0.25 | — | — | 0.5 | — | — | — | — | — | 1.0 |
| NaOH/HCl (pH) | 7.1 | 6.8 | 6.5 | 7.0 | 7.2 | 7.1 | 6.8 | 7.1 | 6.9 | 6.9 | 6.9 |
| Purified Water/WFI | Q.S. | Q.S. | Q.S. | Q.S. | Q.S. | Q.S. | Q.S. | Q.S. | Q.S. | Q.S. | Q.S. |

Penetration enhancers for the vehicles of Tables 1 and II and in compositions described throughout the application may be substituted with:
Alcohols: Ethanol; 1-Propanol; 1-Butanol; 1-Pentanol; 1-Hexanol; 1-Heptanol; 1-Octanol; 1-Nonanol; 1-Undecanol; Oleyl alcohol; 2-Hexanol; 3-Hexanol; 2-Heptanol; 3-Heptanol; 4-Heptanol; 2-Octanol; 3-Octanol; 4-Octanol; 2-Nonanol; 3-Nonanol; 4-Nonanol; 5-Nonanol; cis-3-Penten-1-ol; cis-3-Hexen-1-ol; cis-3-Octen-1-ol; cis-3-Nonen-1-ol; and trans-3-Hexen-1-01;
Amides: trans-Hydroxyproline-Ndecanamide; C-ethylamide; N,N-Dimethylhexanamide; N,N-Dimethylheptanamide; N,N-Dimethyloctanamide; and N,N-Dimethylnonanamide;
Aromatic ring alcohol: Benzyl alcohol; 2-Phenoxyethanol; and 2-Phenylethanol;
Aromatic ring benzoate: Padimate O;
Aromatic ring: hydroxyanisole; Butylated hydroxyanisole; and hydroxyanisole;
Aromatic ring salicylate: 2-Ethylhexyl salicylate; Salicylaldehyde salicylate;
Azone: 1-Butyl-2-azacycloheptanones; 1-Hexyl-2-azacycloheptanones; 1-Octyl-2-azacycloheptanones; Laurocapram (Azone);
Diol: 1,2-Hexanediol; 1,2-Octanediol; and 1-2-Decanediol;
Dioxalane: 2-(1-Butyl)-2-methyl-1,3 dioxolane; and 2-(1-Hexyl)-2-methyl-1,3 dioxolane;
Ester: Isopropyl myristate;
Fatty acid: Decanoic acid; Undecanoic acid; Laurie acid; Tridecanoic acid; Myristic acid; Pentadecanoic acid; Palmitic acid; Stearic acid; Linoleic; Linolenic acid; Oleic acid; and, Ricinoleic acid;
Glucoside: 1-Octyl-β-D-glucopyranoside; and 1-Decyl-β-D-glucopyranoside;
Monoglyceride: 12-Dihydroxypropyl octanoate; and 1,2-Dihydroxypropyl decanoate;
Piperidone: 1-Butyl-2-piperidinone; 1-Hexyl-2-piperidinone; and 1-Octyl-2-piperidinone;
Pyrolidone: 1-Ethyl-2-pyrrolidone; 1-Butyl-2-pyrrolidones; 1-Hexyl-2-pyrrolidinone;
Terpene: Thymol; Menthol; Menthone; Carvacrol; and Cineole;
Triol: 123-Nonanetriol;

Penetration enhancers may also include oils such as niaouli oil, eucalyptus oil, alpinia oxyphylla oil, Turpentine oil, sweet basil oil, tulsi oil, cardamom oil, peppermint oil, fennel oil, black cumin oil, D-limonene, menthol, carvone, geraniol, cineole Transcutol®, DMSO, Labrasol®, propylene glycol, polyethylene glycol, cremophor RH-40, fish oil, phospholipids, oleic acid, isopropyl myristate, oxybutynin, and monolaurate, chitosan, aloe vera, capsaicin, and vitamin E.

Preservatives of the vehicles of Tables I and II and in compositions throughout the application may be substituted with the following preservatives expressed in % w/v or % w/w:
  Na—borate/Boric Acid 1.5%-1.9%;
  Polyhexamthethylene biguanide (PHMB) from 0.0001%-0.02%;
  Parabens (parahydroxy benzoic acid derivatives;
  Phenyl mercuric nitrate;
  benzalkonium chloride 0.004%-0.02%
  benzelthonium chloride up to 0.01%
  chlorhexidine 0.005% to 0.01%
  chlorbutanol up to 0.5%
  methyl paraben 0.03-0.1%
  phenylethyl alcohol up to 0.5%
  phenylmercuric acetate 0.002-0.004%
  phenylmercuric nitrate 0.002-0.004%
  propyl paraben up to 0.01%
  thimerosol up to 0.01%

Table II lists possible compositions of creams and gels for periorbital administration. Table II lists possible vehicle compositions in the form of creams or gels of 3-[(3'-fluoro-4-fluorobiphenyl-3-carbonyl) amino] phenoxyacetic acid isopropyl ester but it is intended that any drug referenced in the specification may be included ("Active Agent"):

TABLE II

| Ingredient | Function | Composition (% w/w) | | | | | | | | |
|---|---|---|---|---|---|---|---|---|---|---|
| | | 1 | 2 | 3 | 4 | 5 | 6 | 7 | 8 | 9 |
| Active Agent | Active | 0.1 | 0.2 | 0.3 | 0.2 | 0.2 | 0.1 | 0.2 | 0.1 | 0.1 |
| PEG 400 | Solubilizer | 20 | 25 | — | 15 | 20 | 25 | 20 | — | — |
| Diethylene glycol monoethyl ether | Solubilizer | 25 | 20 | 15 | 20 | 25 | — | 25 | 25 | 25 |
| Lactic Acid | Solubilizer | 5 | 10 | — | 10 | 5 | 10 | 10 | — | 5 |
| Dimethyl Isosorbide | Solubilizer | — | — | — | — | 15 | — | — | — | — |
| Isopropyl Myristate | Solubilizer | — | — | 10 | — | — | 5 | — | 10 | — |
| Carboxymethyl Cellulose | Thickener | 5 | — | 20 | 10 | 15 | 10 | — | 5 | 25 |
| Hydroxyethyl Cellulose | Thickener | 20 | 25 | 5 | 10 | 15 | 10 | 20 | 5 | — |
| Glycerin | Humectant | 10 | 10 | — | — | — | 10 | 10 | 2 | — |
| EDTA Disodium | Antioxidant | 0.01 | 0.01 | 0.01 | 0.01 | 0.01 | 0.01 | 0.01 | 0.01 | — |
| Citric Acid | Antioxidant | 0.03 | 0.03 | 0.03 | 0.03 | 0.03 | 0.03 | 0.03 | 0.03 | — |
| Propylene Glycol | Penetration Enhancer | 10 | — | — | 20 | 10 | 20 | — | 20 | 15 |
| Oleyl Alchol | Penetration Enhancer | 5 | 3 | 5 | — | 5 | 10 | 15 | — | — |
| Benzyl Alcohol | Preservative | 1.0 | 2.0 | 1.5 | — | 1.0 | 2.0 | 1.5 | 1.0 | — |
| Purified Water | Solubilizer | Q.S. | Q.S. | Q.S. | Q.S. | Q.S. | Q.S. | Q.S. | Q.S. | Q.S. |

The active agent, which may be any drug referenced in the specification, may be present in the following concentrations from a percent w/v or w/w of about 0.01 to about 0.15, from about 0.02 to about 0.15, from about 0.03 to about 0.15, from about 0.04 to about 0.15, from about 0.05 to about 0.15, from about 0.06 to about 0.15, from about 0.07 to about 0.15, from about 0.08 to about 0.15, from about 0.09 to about 0.15, from about 0.1 to about 0.15, from about 0.11 to about 0.15, from about 0.115 to about 0.15, from about 0.120 to about 0.15, and from about 0.125 to about 0.15, from about 0.125 to about 0.145, from about 0.125 to about 0.14, from about 0.02 to about 0.08, from about 0.03 to about 0.08, from about 0.04 to about 0.08, from about 0.05 to about 0.08, from about 0.06 to about 0.08, from about 0.07 to about 0.08, from about 0.02 to about 0.07, from about 0.03 to about 0.07, from about 0.04 to about 0.07, from about 0.05 to about 0.07, from about 0.06 to about 0.07, from about 0.02 to about 0.06, from about 0.03 to about 0.06, from about 0.04 to about 0.06, from about 0.05 to about 0.06, from about 0.02 to about 0.05, from about 0.03 to about 0.05, from about 0.04 to about 0.05, from about 0.02 to about 0.04, from about 0.03 to about 0.04, or from about 0.02 to about 0.03%. In other embodiments, the active agent may be present at about 0.01, 0.02, 0.03, 0.04, 0.05, 0.06, 0.07, 0.08, 0.09, or 0.1, 0.11, 0.12, 0.121, 0.122, 0.125, 0.13, 0.135, 0.140, 0.145, 0.150, 0.155, 0.160, 0.165, 0.170, 0.175, 0.180, 0.185, 0.190, 0.195, 0.2, 0.25, 0.30, 0.35, 0.4, 0.45, 0.5, 0.55, 0.6, 0.65, 0.7, 0.75, 0.8, 0.85, 0.9, 0.95, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5 and 10.0 (% w/v) or (% w/w).

FIG. 1A is a diagrammatic representation of the front of an open eye. The cross-hatched area 10 represents the area for periorbital drug application. The upper eyelid is indicated by 12. The lacrimal gland is indicated by 14. The surface of the eye is shown by 30. FIG. 1B is a diagrammatic representation of the front of a closed eye. The cross-hatched area 10 represents the area for periorbital drug application. The upper eyelid is indicated by the hatched area 12. The approximate demarcation region between the upper eyelid and the periorbital tissue is represented by 32. The lacrimal gland is indicated by 14. The upper eyelid margin and lower eyelid are represented by 28 and 26, respectively. FIG. 1C is a diagrammatic representation of a side view section of the front of an eye. The area for periorbital application is represented by section 10. The area for upper eyelid application is indicated by section 12. The area for lower eyelid application is indicated by section 26. The ocular surface, where ophthalmic drugs are typically applied, is represented by 30. The lacrimal gland is indicated by 14. The chamber angle through which pressure dependent aqueous humor outflow occurs is depicted by 22. The anterior portion of the ciliary body through which pressure independent aqueous humor outflow occurs is depicted by 24.

The composition may be applied to the periorbital skin in a circular manner as shown in FIG. 1A-1C or applied to the periorbital skin (10, FIGS. 1A-1C) above the upper eyelid and below the lower eyelid separately. For delivery of anti-glaucoma agents, the compound formulation should be delivered in an elliptical line (10, FIGS. 1A-1C) that traces the periorbital area. The trabecular meshwork and Schlemm's canal (22, FIG. 1C) are key structures that permit aqueous humor exit from the eye and they reside in the anterior segment chamber angle. The sclera is positioned above the anterior portion of the ciliary body (24, FIG. 1C), which is the site of action for drugs, such as many prostaglandins, that increase pressure independent of uveoscleral outflow (Richter et al., Invest. Ophthalmol. Vis. Sci. 44: 4419-4426, 2003). In order to target the uveoscleral outflow pathway, drug solution or a cream/gel would be applied in an elliptical orbit describing the outer limits of the skin overlying the eye socket (see FIGS. 1A-1B).

A simplistic guide to periorbital application is provided as follows. The upper eyelid, when closed, ends at the top of the cornea, which can be visualized as the top of the underlying structures (e.g. iris and pupil). The same demarcation line applies to the lower eyelid. A practical way to distinguish the eyelid and periorbital area is with a blunt rod about 1 cm wide (e.g. an index finger) held perpendicular to the eye. If one runs an index finger over a closed eye and one can feel only eyeball at the tip of one's finger (rod), then one is in the eyelid region. Keeping the rod or index finger perpendicular, if it is moved it up, down, and to either side, when one feels bone on the side of the rod, then the tip of the rod is in the periorbital region.

Since anti-glaucoma medications would not be applied directly to the ocular surface according to the present invention, nociceptive side effects, ocular surface redness, corneal thinning or thickening, and inflammation associated with eye drops would be reduced or avoided altogether. In the case of the cornea, there would be no need to unnecessarily apply drug over the eyelid (12, FIG. 1B-1C) when treating ocular diseases such as glaucoma and dry eye.

The precise mechanism of action of 3-[(3'-fluoro-4-fluorobiphenyl-3-carbonyl) amino] phenoxyacetic acid in lowering IOP is not known. In applying the drug to the periorbital skin, the drug would pass through the skin in a manner typical for topical application of drugs in dermatology. Thus, there would be immediate contact with the stratum corneum and rapid movement into the epidermis. Thereafter, the dermis would be achieved. The periorbital skin that surrounds the eye socket is "loose" and is not continuously attached to the globe, thereby creating space between the globe and the periorbital skin. This may enhance passage of drug solution from the periorbital skin directly into the underlying globe. Skin in most other body areas is continuously attached to underlying tissue, for example, the underlying tissue of skeletal muscle, subcutaneous fat, and the peritoneum.

In addition to treating glaucomatous diseases, other diseases of the ocular anterior segment and surface (see embodiment 77) may be treated by topical application to the overlying periorbital skin area. "Periorbital" is contrasted with "periocular", the latter term referring to in and around the eyeball. In the case of dry eye diseases and related conditions, drug may be specifically directed over the tear producing lacrimal glands (14, FIGS. 1A-1C). Thus, by applying drug composition between the 12:00 to 2:00 o'clock positions on the right eye and the 10:00 to 12:00 o'clock positions on the left eye (as viewed by a mirror) of the periorbital skin (10, FIG. 1B) overlying the eye sockets, drug may achieve both lacrimal glands (14, FIGS. 1A-1C). The two the lacrimal glands (14) are associated with the upper orbit and are under the upper periorbital skin. Meibomian gland dysfunction may also be treated by application of drug formulation to the overlying orbital skin, namely the upper eyelid margin. The Meibomian gland secretes a lipid-containing lubricating solution and its dysfunction has been implicated in dry eye conditions and related symptomology and has been suggested to contribute to blepharitis. In a different therapeutic sense, "puffy eyes" from periorbital fat deposition and/or edema and periorbital redness and suboptimal appearance may be treated by periorbital skin (10) application to areas overlying the enlarged and/or affected tissue areas. These are intended as non-limiting examples of ocular periorbital delivery. In addition to ocular application, the metered/measured topical delivery of drugs, by using a radial or vertically operated ratchet, may be extended to other areas to treat conditions such as peripheral neuronal conditions and for reduction of submental fat and cellulite.

Drug application to the upper eyelid (12) surface has been employed or suggested as a method of treating eyelid diseases (U.S. Pat. No. 7,655,625 B2, U.S. Pat. No. 8,900,626 B2, EP application 2720748). Compositions containing muscle fasciculating agents and vasoactive compounds have been suggested for sustained release of drugs for treating ocular and other diseases involving both local and systemic bioavailability (U.S. Pat. No. 8,685,439, EP application 2056809, EP application 2493475). Application to the upper eyelid (12), which closes over the globe, is not optimal for delivery of drug to the surface of the globe or the anterior segment tissues. Application to the upper eyelid would favor delivery to the cornea and conjunctiva, with a resultant greater likelihood of side effects. The eyelid (12) may be regarded as a separate structure distinct from the upper eyelid (WO application 201445300 A2).

Any reference made to patents and printed publications throughout this specification is individually incorporated herein by reference in its entirety. It is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

Example I

The experimental protocol was as follows:
Day 1; 8 Cynomolgus monkeys, which are the favored animal model for glaucoma studies, were assigned to the study. Intraocular pressure was measured in both eyes. The 6 animals with the highest intraocular pressure were selected for study.
Animal Information

| NO. | Animal ID | Spice | Sex | Age (years) | B.W. (Kg) |
|---|---|---|---|---|---|
| 1 | 052267 | Cynomolgus | Female | 10 | 5.6 |
| 2 | 082272 | Cynomolgus | Female | 7 | 3.4 |
| 3 | 082150 | Cynomolgus | Female | 7 | 6.6 |
| 4 | 072270 | Cynomolgus | Female | 8 | 4.7 |
| 5 | 072271 | Cynomolgus | Female | 8 | 4.5 |
| 6 | 052268 | Cynomolgus | Female | 10 | 3.8 |

All Cynomolgus monkey experiments adhered to the ARVO statement for the Use of Animals in Ophthalmic and Vision Research and in accordance with the recommendations of Guide for the Care and Use of Laboratory Animals.

Day 2 Intraocular pressure was measured in both eyes of the 6 selected animals. Before dosing the monkeys, the delivery of vehicle (Polyethylene glycol 400) and the compound (3-[(3'-fluoro-4-fluorobiphenyl-3-carbonyl) amino] phenoxyacetic acid isopropyl ester from the roller-ball applicator bottle was checked by rolling it along a solid surface (e.g. glass or plastic) until the liquid flowed freely from the roller-ball. The formulation of (3-[(3'-fluoro-4-fluorobiphenyl-3-carbonyl) amino] phenoxyacetic acid isopropyl ester was applied immediately afterwards by rolling the roller-ball slowly around the skin surrounding the left eye socket of each monkey. The roller-ball was rolled around this area 5 times for each monkey. The same drug application procedure was performed for the vehicle (Polyethylene glycol 400) to the right eye socket of each monkey. Intraocular pressure was measured in both eyes at 3 hours post-drug and vehicle application and again at 5 hours post-drug and vehicle application. The conjunctivae of both eyes were checked for redness at the end of the daily experimental period.

Day 3; Repeat the operation of Day 2.
Day 4; Repeat the operation of Day 2.
Day 5; Repeat the operation of Day 2.
Days 6 and 7, no drug administered.
Day 8; Intraocular pressure was measured in both eyes and the conjunctivae were checked for redness/hyperemia.
Day 15; Intraocular pressure in was measured in both eyes and the conjunctivae were checked for redness/hyperemia.

Figure 2:
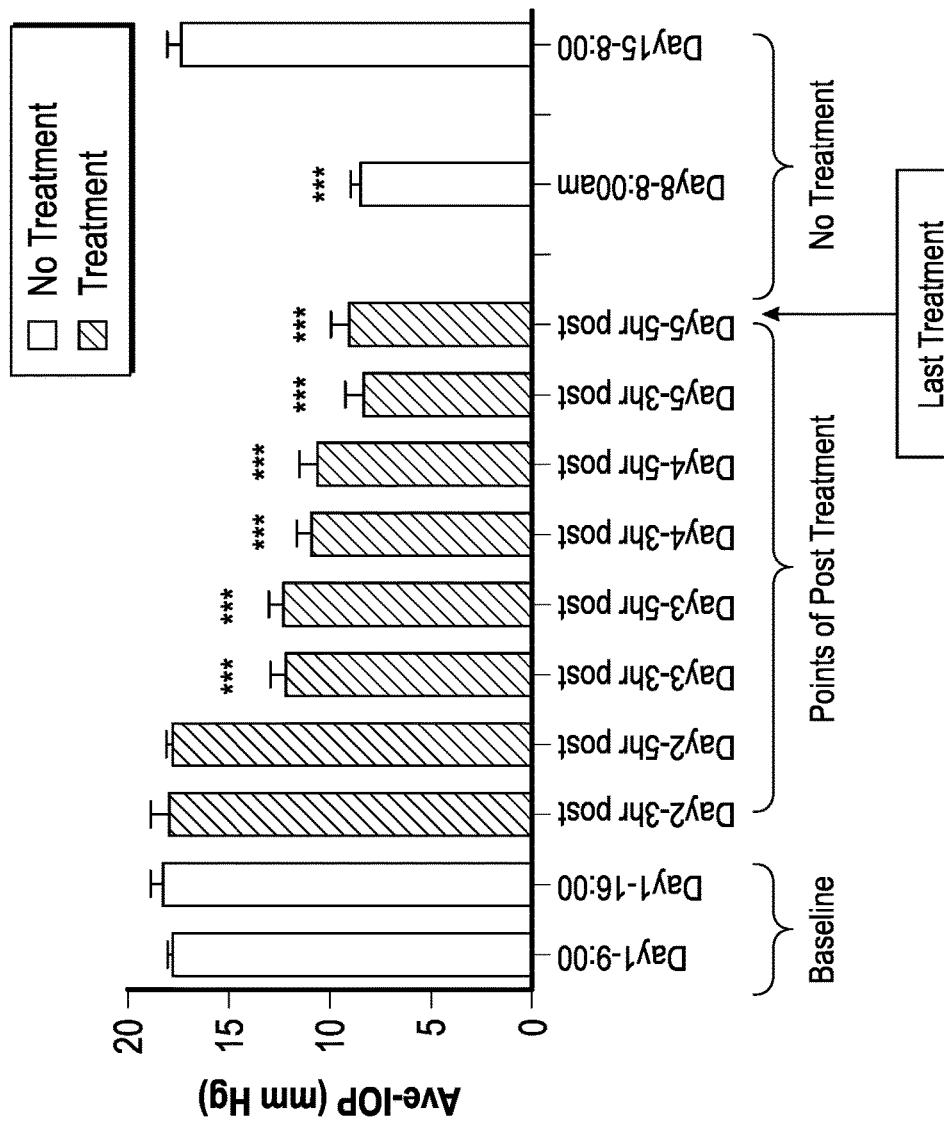

The data demonstrate that IOP was effectively lowered from normal baseline levels to significantly lower levels and IOP remained low for several days after the drug was administered (see FIG. 2). This is very unusual as most IOP lowering drugs are administered daily in order to continuously lower IOP. The following results were obtained and are provided in the following graph. Statistically significant reductions in intraocular pressure were achieved for the drug, Table III and FIG. 2.

TABLE III

Effect of Ocular Pressure (Left Eye)

| Treatment | Mean | SD | n |
|---|---|---|---|
| Day 1-9:00 (Baseline) | 17.8 | 0.7 | 6 |
| Day 1-16:00 (Baseline) | 18.3 | 1.6 | 6 |
| Day 2-3 hr post | 18.0 | 2.1 | 6 |
| Day 2-5 hr post | 17.8 | 0.8 | 6 |
| Day 3-3 hr post | 12.2 | 1.8 | 6 |
| Day 3-5 hr post | 12.3 | 1.7 | 6 |
| Day 4-3 hr post | 10.9 | 1.6 | 6 |
| Day 4-5 hr post | 10.6 | 2.3 | 6 |
| Day 5-3 hr post | 8.4 | 2.1 | 6 |
| Day 5-5 hr post | 9.1 | 2.0 | 6 |
| Day 8-8:00am | 8.5 | 1.3 | 6 |
| Day 15-8:00 | 17.4 | 1.6 | 6 |

Example II

A 55-year-old African American male suffers from ocular hypertension and the patient's ophthalmologist is concerned his condition could progress to glaucoma if the patient's elevated intraocular pressure is not brought down to normal levels. The patient applies a solution of 0.1% w/v 3-[(3'-fluoro-4-fluorobiphenyl-3-carbonyl)amino] phenoxyacetic acid isopropyl ester (Formula 5, Table I) to the periorbital skin around each eye by use of a roller device applicator to each eye for three days. After day 2, the patient's IOP will begin to drop to normal levels. After Day 3, the patient will then administer the drug once a week to the patient's periorbital skin around each eye. The patient's IOP will fall to normal levels and stays at normal levels as long as the patient continues to administer the solution once a week.

Example III

A 72-year-old Caucasian female suffers from open angle glaucoma with elevated IOP. After an eye exam, the patient's ophthalmologist prescribes a cream comprising 0.2% w/w of 3-[(3'-fluoro-4-fluorobiphenyl-3-carbonyl) amino] phenoxyacetic acid isopropyl ester (Composition 4, Table II). The patient will apply the cream once a week around her periorbital skin of both eyes and 24 hours after the first application the patient's IOP lowers to normal levels. The patient's IOP remains at normal levels so long as the patient continues to administer the composition weekly.

Example IV

A 41-year-old Asian male is diagnosed with elevated IOP approaching 27 mm Hg. The patient applies a 0.2% w/w

TABLE IV

Ocular Surface Hyperemia Assessment

| | | | | Conjunctival Congestion | | | | | | | | | | | |
|---|---|---|---|---|---|---|---|---|---|---|---|---|---|---|---|
| Group | Animal ID | Eyes | Compounds | 150406 (9:00) Baseline | 150406 (16:00) baseline | 150407 (12:00) | 150407 (14:00) | 150408 (12:00) | 150408 (14:00) | 150409 (12:00) | 150409 (14:00) | 150410 (12:00) | 150410 (14:00) | 150413 (8:00) | 150420 (8:00) |
| Group 1 (n = 6) | 052267 | Left eyes | Phenoxyacetic Acid | 0 | 0 | 0 | 0 | 0 | 0 | 0 | 0 | 0 | 0 | 0.6 | 0 |
| | 082272 | | | 0 | 0 | 0 | 0 | 0 | 0 | 0 | 0 | 0 | 0 | 0 | 0 |
| | 082150 | | | 0 | 0 | 0 | 0 | 0 | 0 | 0 | 0 | 0 | 0 | 0.5 | 0 |
| | 072270 | | | 0 | 0 | 0 | 0 | 0 | 0 | 0 | 0 | 0 | 0 | 0 | 0 |
| | 072271 | | | 0 | 0 | 0 | 0 | 0 | 0 | 0 | 0 | 0 | 0 | 0 | 0 |
| | 052268 | | | 0 | 0 | 0 | 0 | 0 | 0 | 0 | 0 | 0 | 0 | 0 | 0 |
| Group 2 (n = 6) | 052267 | Right eyes | Vehicle | 0 | 0 | 0 | 0 | 0 | 0 | 0 | 0 | 0 | 0 | 0 | 0 |
| | 082272 | | | 0 | 0 | 0 | 0 | 0 | 0 | 0 | 0 | 0 | 0 | 0 | 0 |
| | 082150 | | | 0 | 0 | 0 | 0 | 0 | 0 | 0 | 0 | 0 | 0 | 0 | 0 |
| | 072270 | | | 0 | 0 | 0 | 0 | 0 | 0 | 0 | 0 | 0 | 0 | 0 | 0 |
| | 072271 | | | 0 | 0 | 0 | 0 | 0 | 0 | 0 | 0 | 0 | 0 | 0 | 0 |
| | 052268 | | | 0 | 0 | 0 | 0 | 0 | 0 | 0 | 0 | 0 | 0 | 0 | 0 |

Comments:
HYPEREMIA
| SCORE | APPEARANCE OF CONJUNCTIVAL VIA VIDEO |
|---|---|
| 0 | Normal Appearance |
| 0.5 | Very Slight Redness or Dilation of Conjunctival Vessels |
| 1 | More Obvious Redness or Dilation of Conjunctival Vessels |
| 2 | Whole Conjunctiva Exhibiting Pronounced Red Coloration. Visual Clarification of Individual Conjunctival Vessels Difficult. |
| 3 | Whole Conjunctiva Exhibiting Pronounced Red Coloration. Visual Clarification of Individual Iridial Vessels Impossible. Accompany Conjunctival Edema. |

As shown in Table IV, there was almost no surface hyperemia in any of the Cynomolgus monkeys with the exception of very slight redness on Day 7 in two monkeys. cream (Composition 2, Table II) of 3-[(3'-fluoro-4-fluorobiphenyl-3-carbonyl) amino] phenoxyacetic acid isopropyl ester to the periorbital skin of both eyes above the upper eyelid and below the lower eyelid. The patient applies the cream using a dispensing device, which dispenses a predetermined dose of composition to the periorbital skin. The patient will continue applying the emulsion once a week to control IOP.

Example V

A 61-year-old Caucasian male suffers from elevated IOP that is not controllable with monotherapy of a beta-blocker. The patient administers 0.3% w/w cream (Composition 3, Table II) of 3-[(3'-fluoro-4-fluorobiphenyl-3-carbonyl) amino] phenoxyacetic acid isopropyl ester to the periorbital skin of both eyes by dispensing the cream from a dispenser which dispenses about 50 μg of the cream around each eye. This will be accomplished by administering the cream to the periorbital skin of each twice, after waiting five minutes between the first and second administration. The patient then applies the cream once a day for four days and then once a week thereafter. The patient's IOP returns to normal levels and maintains at normal levels so long as the cream is applied once a week.

Example VI

A 72 year old African American female with unusually high IOP and symptoms of glaucoma applies the 0.03% w/v solution (Formula 3, Table I) of 3-[(3'-fluoro-4-fluorobiphenyl-3-carbonyl)amino] phenoxyacetic acid isopropyl ester to the periorbital skin of both eyes and within 24 hours, her IOP will return to near normal levels. A week later, the patient applies another dose her periorbital skin and her IOP lowers to normal levels.

Example VII

A 27-year-old Caucasian female suffers from dry eye that is not responsive to treatment with artificial tears. The patient applies a cream of 0.1% w/w cyclosporine (Composition 6, Table II) to the periorbital skin of both eyes once a week which provides relief from the dry eye symptoms.

Example VIII

A 7-year-old Asian pediatric patient suffers from bacterial conjunctivitis in his right eye. A 0.3% w/w ciprofloxacin cream (Composition 3, Table II) is added to the periorbital skin of the right eye daily until the bacterial infection disappears.

Example IX

A 73-year-old African American male is suffering from ocular/pain inflammation after cataract surgery. The patient applies a 0.1% w/v solution of prednisolone (formula 5, table 1) once a day for five days to the periorbital skin of both eyes which reduces the pain and inflammation.

Example X

An eighty year old Caucasian man suffers from glaucoma and elevated intraocular pressure and applies a 0.02% w/v drop of (Formula 2, Table I) of 3-[(3'-fluoro-4-fluorobiphenyl-3-carbonyl)amino] phenoxyacetic acid isopropyl ester once a week to the periorbital skin of both eyes once a week for the treatment of glaucoma and elevated intraocular pressure. After two days, the patient's intraocular pressure returns to normal levels.

The invention claimed is:

1. A method of lowering intraocular pressure in a patient suffering from elevated intraocular pressure comprising administering a therapeutically effective amount of a composition comprising 3-[(3'-fluoro-4-fluorobiphenyl-3-carbonyl) amino] phenoxyacetic acid isopropyl ester to the periorbital skin of an eye of the patient wherein the 3-[(3'-fluoro-4-fluorobiphenyl-3-carbonyl) amino] phenoxyacetic acid isopropyl ester is applied as a topical composition having a concentration of about 0.01% to about 10% (w/w).

2. The method of claim 1 wherein the composition comprising 3-[(3'-fluoro-4-fluorobiphenyl-3-carbonyl) amino] phenoxyacetic acid isopropyl ester is applied to the periorbital skin of each eye of the patient once every seven days to effectively lower intraocular pressure.

3. The method of claim 1 wherein the composition comprising 3-[(3'-fluoro-4-fluorobiphenyl-3-carbonyl) amino] phenoxyacetic acid isopropyl ester is a solution.

4. The method of claim 1 wherein the composition comprising 3-[(3'-fluoro-4-fluorobiphenyl-3-carbonyl) amino] phenoxyacetic acid isopropyl ester is an emulsion.

5. The method of claim 1 wherein the composition comprising 3-[(3'-fluoro-4-fluorobiphenyl-3-carbonyl) amino] phenoxyacetic acid isopropyl ester is a cream.

6. The method of claim 1 wherein the composition comprising 3-[(3'-fluoro-4-fluorobiphenyl-3-carbonyl) amino] phenoxyacetic acid isopropyl ester lowers elevated intraocular pressure for up to fourteen days with a single administration.

7. The method of claim 1 wherein the composition is administered from a device which releases a preselected dosage in an approximate uniform manner onto the periorbital skin of the patient.

8. The method of claim 1 wherein the composition comprising 3-[(3'-fluoro-4-fluorobiphenyl-3-carbonyl) amino] phenoxyacetic acid isopropyl ester is administered to the periorbital skin of the individual to at least one eye.

9. The method of claim 8 wherein the method comprises administering the composition to the periorbital skin above the upper eyelid and below the lower eyelid.

10. A method of lowering intraocular pressure in a patient suffering from glaucoma comprising administering a therapeutically effective amount of a composition comprising 3-[(3'-fluoro-4-fluorobiphenyl-3-carbonyl)amino] phenoxyacetic acid isopropyl ester to the periorbital skin of an eye of the patient wherein the 3-[(3'-fluoro-4-fluorobiphenyl-3-carbonyl)amino] phenoxyacetic acid isopropyl ester is applied as a topical composition having a concentration of about 0.01% to about 10% (w/w).

11. The method of claim 10 wherein the composition is applied daily to the periorbital skin of the patient for up to five days and then once every seven days thereafter thereby lowering IOP to normal levels.

12. The method of claim 10 wherein the composition is in the form of one selected from the group consisting of a solution, an emulsion, a dispersion and a suspension.

13. The method of claim 10 wherein the composition is applied to the periorbital skin of the eye by use of a delivery device wherein the patient applies the composition at least one time to the periorbital skin of each eye which constitutes a single administration.

14. The method of claim 10 wherein the composition is applied to the periorbital skin of the eye by use of a delivery device wherein the patient applies the composition at least two times to the periorbital skin of each eye which constitutes a single administration.

15. The method of claim 10 wherein the composition is in the form of one selected from the group consisting of a topical cream, gel, hydrogel, organogel, xerogels, lotion, nanocomposite hydrogels, foam, and a solution in an organic solvent.

16. The method of claim 15 wherein the composition is applied daily to the periorbital skin of the patient for up to five days and then once every seven days thereafter thereby lowering IOP to normal levels.

17. The method of claim 16 wherein the composition is a cream and is applied to the periorbital skin which constitutes a single administration.

18. The method of claim 17 wherein the cream is applied to the periorbital skin of both eyes before sleeping at night once selected from the group consisting of every five, six or seven days.

19. A method of lowering intraocular pressure to normal levels in a patient suffering from elevated intraocular pressure comprising administering a therapeutically effective amount of a composition comprising 3-[(3'-fluoro-4-fluorobiphenyl-3-carbonyl)amino] phenoxyacetic acid isopropyl ester to the periorbital skin of an eye of the patient wherein the 3-[(3'-fluoro-4-fluorobiphenyl-3-carbonyl)amino] phenoxyacetic acid isopropyl ester is applied as a topical composition having a concentration of about 0.01% to about 10% (w/w).

20. The method of claim 19 wherein the composition is applied every seven days and lowers IOP to normal levels.

21. The method of claim 20 wherein the patient has lower incidents of hyperemia and corneal thickening than the patient would experience if the composition was applied topically to the front of the eye by a topical drop in the same dosage and frequency of administration.

22. The method of claim 20 wherein IOP is maintained at normal levels so long as the patient continues to apply the composition to the periorbital skin once a week.

23. A method of lowering IOP in patients with elevated IOP or glaucoma to achieve an IOP between 12-21 mm Hg by applying a therapeutically effective amount of a composition to the periorbital skin of a patient wherein the composition comprises 3-[(3'-fluoro-4-fluorobiphenyl-3-carbonyl)amino] phenoxyacetic acid isopropyl ester in a concentration of about 0.01% to about 10% (w/w).

24. The method of claim 23 wherein the composition is in a liquid form and is applied by a roller device to the periorbital skin.

25. The method of claim 24 wherein the roller device applies the composition to the periorbital skin of the patient around each eye.

26. The method of claim 25 wherein the amount applied to the periorbital skin of the patient is selected by the patient or physician before administration.

27. The method of claim 25 wherein the composition is applied initially for a duration of one selected from the group of one day, two days, three days, four days and five days consecutively and then once a week thereafter.

28. The method of claim 27 wherein the composition is applied for five days consecutively and then once a week thereafter and the composition maintains IOP to normal levels.

29. The method of claim 28 wherein the patient experiences less side effects than the same composition that is applied topically to the eye daily for five days consecutively and then once a week thereafter.

* * * * *

UNITED STATES PATENT AND TRADEMARK OFFICE
CERTIFICATE OF CORRECTION

PATENT NO.         : 9,820,954 B2
APPLICATION NO.    : 14/829789
DATED              : November 21, 2017
INVENTOR(S)        : David Frederick Woodward et al.

It is certified that error appears in the above-identified patent and that said Letters Patent is hereby corrected as shown below:

In the Specification

Column 3, Lines 40-45 corrected compound should read as shown below:

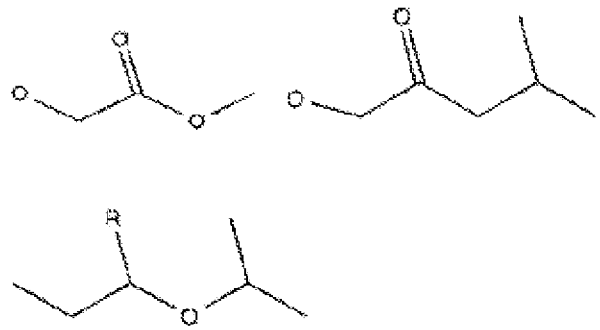

Column 7, Lines 1 and 2 "The EP2 agonist is 3-[(3'–fluoro-fluorobiphenyl-3-carbonyl" should read --The EP2 agonist is 3-[(3'–fluoro-4-fluorobiphenyl-3-carbonyl--.

Column 9, Line 34 "wherein the $EP_1$" should read --wherein the $EP_2$--.

Column 13, Lines 64,65 "Sympathomkimetics phen ytpropanolamine" should read --sympathomimetics phenylpropanolamine--.

Column 13, Line 67 "iprindoie" should read --iprindole--.

Column 14, Line 11 "bitolteroi" should read --bitolterol--.

Column 14, Line 12 "carmoterot" should read --carmoterol--.

Column 14, Line 13 "trimetoquinot" should read --trimetoquinol--.

Signed and Sealed this
Nineteenth Day of June, 2018

Andrei Iancu
*Director of the United States Patent and Trademark Office*

CERTIFICATE OF CORRECTION (continued)
U.S. Pat. No. 9,820,954 B2

Column 14, Lines 13-14 "desformoterot" should read --desformoterol--.

Column 15, Line 31 "E2 receptor" should read --$EP_2$ receptor--.

Column 16, Line 52 "sulfic acid" should read --sulfonic acid--.

Column 16, Line 55 "glycolic acid, hemisulfic acid, heptanoic acid, hexanoic acid" should read --glycolic acid, heptanoic acid, hexanoic acid--.

Column 16, Line 61 "pelargonic" should read --pelargonic acid--.

Column 19, Line 39 "Amides: trans-Hydroxyproline-Ndecanamide" should read --Amides: trans-Hydroxyproline-N-decanamide--.

Column 25, Line 15 "the following graph" should read --Fig. 2 and Table III--.